Dec. 17, 1963 H. C. SWIM ETAL Plant Pat. 2,326
ROSE PLANT
Filed Nov. 13, 1962
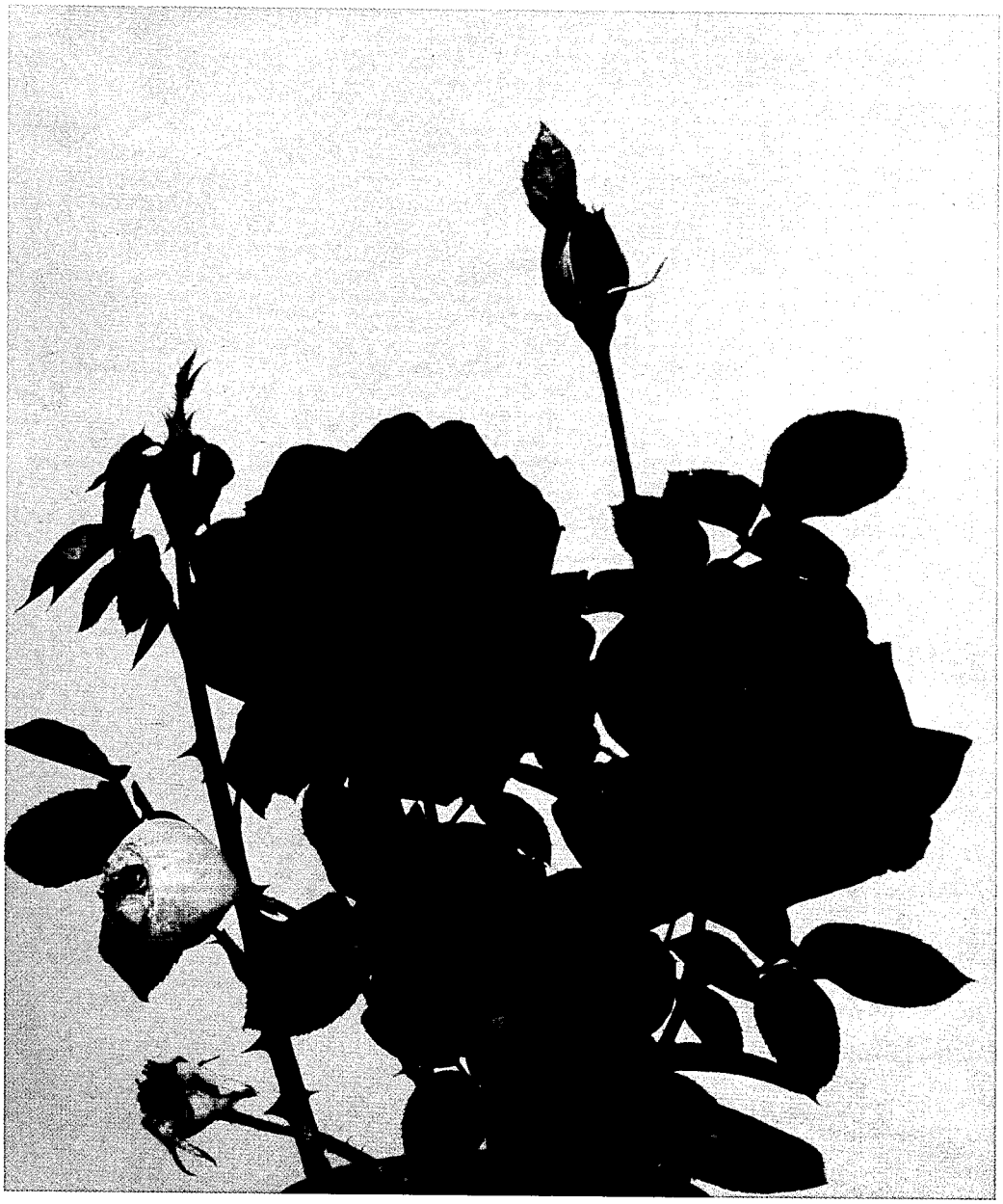
Inventors.
H. C. Swim and
O. L. Weeks
By: Robb & Robb
Attorneys United States Patent Office Plant Pat. 2,326
Patented Dec. 17, 1963

2,326
ROSE PLANT

Herbert C. Swim, Ontario, and O. L. Weeks, Chino, Calif., assignors to Weeks Wholesale Rose Grower, Chino, Calif.

Filed Nov. 13, 1962, Ser. No. 237,414
1 Claim. (Cl. Plt.—21)

The present invention relates to a new and distinct variety of rose plant of the hybrid tea class, which was originated by us by crossing the variety "Chrysler Imperial" (Plant Patent No. 1167) with the variety "Charles Mallerin" (Plant Patent No. 933).

As the result of this breeding, we have produced a new rose variety having the following unique combination of characteristics which are outstanding therein and which distinguish it from its parents, as well as from all other varieties of which we are aware:

(1) Vigorous, bushy and free-branching habits of plant growth;

(2) Moderately abundant foliage and good persistence thereof;

(3) Good balance and stretch of the flower stems;

(4) Large flower size, said flowers having very double petalage and good petal substance;

(5) A distinctive and attractive Deep, Dark Red general color tonality of the flowers;

(6) A strong combination of damask and tea fragrance; and (7) Long-lasting qualities of the flowers both on the plant and as cut flowers.

In comparison with its seed parent, "Chrysler Imperial," the caliper differentiation between the base of the stems and their apex, or juncture of the stems with the peduncle, is substantially less in the case of our new variety than in this parent, and there is a substantially greater average length of the stems in the new variety so that the combination of these features gives a better appearance of balance between the stems and flowers than is found in this parent; the new variety has substantially greater petal substance which gives the flowers a longer-lasting quality both on the plant and when cut, this improved substance being readily evident by both touch and visual observation; after the outer flower petals have opened on the new variety, the intermediate petals usually are found with their tips folded over the tips of the remaining petals, which only rarely, if ever, occurs in the case of the parent variety; and the flowers of the new variety have a substantially deeper and darker color in both the bud and open flower stage than is the case of the flowers of "Chrysler Imperial," thereby being easily distinguishable at a glance.

As compared with the pollen parent, "Charles Mallerin," the new variety is more heavily foliaged and the foliage is more persistent in comparison with the sparse and early deciduous foliage of this parent; the habit of growth is more regular and more well-balanced than the irregular and unbalanced habit of this parent, with the new variety branching freely and being quite bushy in comparison with the sparsely branching habit and open appearance of the plant of the parent variety; the new variety has greater flower petalage, ranging from 40 to 55 petals, as compared with 35 to 40 petals in the case of this parent; and the flowers of the new variety are full and high-centered at maturity, as compared with the flat and open flowers of "Charles Mallerin."

Asexual reproduction of our new variety by budding, as performed at Chino, California, shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with the Nickerson Color Fan, published by Munsell Color Company, Incorporated, of Baltimore, Maryland, except where general color terms of ordinary dictionary significance are obvious:

Type: Bush; outdoor; seedling; for cut flowers, garden decoration and exhibition.

Class: Hybrid tea.

Breeding: Seedling.

*Seed parent.*—"Chrysler Imperial."

*Pollen parent.*—"Charles Mallerin."

Propagation: Holds its distinguishing characteristics through succeeding propagations by budding.

*Flower*

Locality where grown and observed: Chino, California.

Flowers borne: Usually singly, but sometimes several on basal stems; on stems of normal strength and medium length.

Quantity of bloom: Free, outdoors.

Continuity: More or less continuous during growing season.

Fragrance: Strong. Nature—a combination of damask and tea.

Bud:

*Peduncle.*—Medium length; medium caliper; from slightly bending to erect; almost smooth, except for few stipitate glands. Color—from Light to Medium Yellowish Green.

*Before calyx breaks.*—Size—medium. Form—pointed; with a conspicuous neck; with foliaceous appendages on the surface of the bud; with more or less slender, much-cut foliaceous parts extending beyond the tip of the bud equal to ¼ or more of its length. Color—between Deep Purplish Red, Plate 10RP3/10 and Black.

*As calyx breaks.*—Color—between Deep Purplish Red, Plate 10RP3/10 and Black.

*As first petal opens.*—Size—large. Form—short; pointed ovoid. Color—outside—predominantly between Deep Purplish Red, Plate 10RP3/10 and Dark Red, Plate 2.5R3/7, with some overlay of near Black. Inside—small spot of Brilliant Greenish Yellow, Plate 7.5Y9/8 about point of attachment, with remainder of lower half of petal nearly Deep Purplish Red, Plate 10RP3/10, but more brilliant, and with upper half of petal being the same basic color, but overlaid strongly with Black.

*Opening.*—Opens up well.

Bloom:

*Size (when fully open).*—Large; from 4 inches to 5½ inches.

*Petalage.*—Very double; from 40 to 55 petals; arranged more or less regularly, usually with no stamens showing.

*Form.*—Full and high-centered at first, and remaining so; petals being rolled outward slightly along upper half of margins adjacent to apex, giving apex more accentuation; flower form remains remarkably constant throughout its life after once fully opening.

Petals:

*Texture.*—Very thick; leathery. Inside—velvety. Outside—satiny.

*Shape.*—Outside—nearly round, with apex inconspicuous or wanting. Intermediate—broadly obovate, with apex inconspicuous or wanting, and with one notch. Inside—slenderly obovate-cuneate; irregularly scalloped; with apex notched; often some wrinkled.

This description of a newly opened flower was made from a rose grown outdoors during the month of October at Chino, California:

*Color.—Outer petal*—outside surface: Between Deep Purplish Red, Plate 10RP3/10 and Dark Red, Plate 2.5R3/7, with some overlay of Black or very Deep Purple on upper portion; inside surface: small spot of Brilliant Greenish Yellow, Plate 7.5Y9/8 about point of attachment, with remainder of lower half of petal near Deep Purplish Red, Plate 10RP3/10, and with upper half of petal being same basic color, but overlaid strongly with a very Deep Purple or Black. *Intermediate petal*—outside surface: between Deep Purplish Red, Plate 10RP3/10 and Strong Purplish Red, Plate 10RP4/12; inside surface: small spot of Brilliant Greenish Yellow, Plate 7.5Y9/8 about point of attachment, with remainder of petal on lower ⅖ between Dark Red, Plate 2.5R3/7 and Deep Purplish Red, Plate 10RP3/10, and with upper ⅗ of petal near Deep Purplish Red, Plate 10RP3/10, but deeper with overlay of Deep Purple. *Inner petal*—outside surface: near Dark Red, Plate 2.5R3/7, but very slightly brighter and lighter; inside surface: very small spot of Brilliant Greenish Yellow, Plate 7.5Y9/8 at point of attachment, with remainder of petal having basic color of Deep Purplish Red, Plate 10RP3/10, but overlaid with Dark Red, Plate 2.5R3/7; the velvety nap-like surface reflects different shades and intensities of Red or Purple depending on the angle of light incidence.

This description was made from a rose that was open for three days outdoors during the month of October at Chino, California:

*Color.—Outer petal*—outside surface: small spot of Brilliant Greenish Yellow, Plate 7.5Y9/8 at base, with central area of petal near Strong Purplish Red, Plate 10RP4/12, and color along margins and at apex being between Dark Red, Plate 2.5R3/7 and Deep Purplish Red, Plate 10RP3/10; inside surface: small spot between Brilliant Yellow, Plate 2.5Y9/9 and White at base, with remainder of petal near Deep Purplish Red, Plate 10RP3/10, but with varying degrees of Purple overlay about margins and at apex. *Inner petal*—outside surface: very small spot of near Brilliant Yellow, Plate 5Y9/9 at base, with remainder of petal near Deep Purplish Red, Plate 10RP3/10; inside surface: small spot near White at base, with remainder of petal having basic color near Deep Purplish Red, Plate 10RP3/10, but overlaid with Deep Purple of greater intensity progressing toward margins and apex.

*General color effect.—Newly opened flower*—basically between Dark Red, Plate 2.5R3/7, and Deep Purplish Red, Plate 10RP3/10, but overlaid with Deep Purple, giving a much darker effect than either of these colors. *3-days open*—basically between Dark Red, Plate 2.5R3/7 and Deep Purplish Red, Plate 10RP3/10, but as in the newly opened flower, overlaid with a Deep Purple, giving a much darker effect, said Purple color becoming more pervading in the 3-days open flowers than in the newly opened flowers.

*Behavior.*—Drop off cleanly; becomes strong Purple with age.

*Flower longevity.*—on bush in garden—5 or 6 days during October. Cut roses grown outdoors and kept at living-room temperatures—4 or 5 days during October.

*Reproductive Organs*

Stamens: Medium quantity; arranged regularly about pistils; occasionally mixed with petaloids.

Filaments: Medium length; most with anthers. Color—White at base, but Reddish on upper ⅔.

Anthers: Medium size; open at various times. Color—Yellow margins and Reddish centers.

Pollen: Moderately abundant. Color—Gold.

Pistils: From medium number to many.

Styles: Uneven; from medium length to long; thin; loosely bunched.

Stigma: Color—Whitish-translucent.

Ovaries: Most enclosed in, but some protruding from, calyx.

Hips: Globular; without conspicuous neck; smooth; somewhat ribbed; walls thick and fleshy. Color—from Orange to Russet, with some Crimson markings.

Sepals: Permanent where open pollinated; medium length; more or less straight; spear-shaped.

Seeds: Many; from small to large; up to 30 or more in number.

*Plant*

Foliage:

*Leaves.*—Compound of 3–7 leaflets; moderately abundant; medium size; moderately heavy; leathery; non-glossy.

*Leaflets.*—Shape—ovate, with apex from acute to acuminate. Base—from rounded to cuneate and sometimes asymmetrical. Margin—simply serrate, with occasional double serration.

*Color.*—Mature—upper surface: Dark Green; under surface: Normal Grey-Green. Young—upper surface: Green, overlaid with Dark Red; under surface: Green, overlaid with Dark Red.

*Rachis (the supporting stem of the compound leaf).*—Medium caliper and weight. Upper side—grooved; hairy; ridges lined with stipitate glands. Under side—moderately hairy and prickly; numerous stipitate glands.

*Stipules.*—Medium length; very narrow; with points of medium length turning out at an angle of less than 45°.

*Disease resistance.*—Average resistance to powdery mildew when compared with other Red roses grown under comparable conditions at Chino, California, but somewhat less than average resistance to this disease when compared with roses of other color classes as grown under comparable conditions at Chino, California.

Growth:

*Habit.*—Bushy; upright; much-branched.

*Growth.*—Vigorous.

*Canes.*—From medium to heavy.

*Main stems.*—Color—Dull Grey-Green. Large prickles: many, medium length, mostly straight but occasionally slightly hooked downward, base varies from medium length to short, medium width; color: Brown. Small prickles: several; color: Brown. Hairs: none.

*Branches.*—Color—dull Grey-Green. Large prickles—many, medium length, straight, with base ranging from short to medium length, medium width. Color—Brown. Small prickles—few. Color—Brown. Hairs—none.

*New shoots.*—Color—Green, with Red overlay. Large prickles—many; medium length; from straight to slightly hooked downward; with base ranging from medium length to short; medium width. Color—Reddish. Small prickles—few. Color—Reddish. Hairs—none.

We claim:

A new and distinct variety of rose plant of the hybrid tea class, substantially as herein shown and described, characterized particularly as to novelty by the unique combination of vigorous, bushy and free-branching habits of plant growth, moderately abundant foliage and good persistence thereof, good balance and stretch of the flower stems, large flower size, with the flowers having very double petalage and good petal substance, an attractive and distinctive deep Dark Red general color tonality of the flowers, a strong combination of damask and tea flower fragrance, and long-lasting qualities of the flowers both on the plant and as cut flowers.

No references cited.